United States Patent
Togawa (10) Patent No.: US 9,587,807 B2
(45) Date of Patent: Mar. 7, 2017

(54) LIGHTING APPARATUS

(71) Applicant: CCS INC., Kyoto-shi, Kyoto (JP)

(72) Inventor: Takuzo Togawa, Kyoto (JP)

(73) Assignee: CCS INC., Kyoto (JP)

( * ) Notice: Subject to any disclaimer, the term of this patent is extended or adjusted under 35 U.S.C. 154(b) by 0 days.

(21) Appl. No.: 14/786,792

(22) PCT Filed: Apr. 28, 2014

(86) PCT No.: PCT/JP2014/061833
§ 371 (c)(1),
(2) Date: Oct. 23, 2015

(87) PCT Pub. No.: WO2014/178366
PCT Pub. Date: Nov. 6, 2014

(65) Prior Publication Data
US 2016/0084479 A1   Mar. 24, 2016

(30) Foreign Application Priority Data

May 2, 2013 (JP) .................................. 2013-096859

(51) Int. Cl.
*F21V 19/00* (2006.01)
*F21V 15/01* (2006.01)
(Continued)

(52) U.S. Cl.
CPC ............ *F21V 15/01* (2013.01); *F21V 19/003* (2013.01); *F21V 23/02* (2013.01);
(Continued)

(58) Field of Classification Search
CPC ........ F21V 15/01; F21V 23/02; F21V 29/507; F21V 23/001; G01N 21/8806;
(Continued)

(56) References Cited

U.S. PATENT DOCUMENTS 4,523,258 A * 6/1985 Morse ................. F21V 33/0008
362/108
5,920,643 A * 7/1999 White ................. G01N 21/8806
362/249.04

(Continued)

FOREIGN PATENT DOCUMENTS

DE   103 50 913 A1   6/2005
EP   1 691 592 A1    8/2006

(Continued)

OTHER PUBLICATIONS

Jun. 17, 2014 Written Opinion of the International Searching Authority issued in International Patent Application No. PCT/JP2014/061833.

(Continued)

*Primary Examiner* — Bryon T Gyllstrom
(74) *Attorney, Agent, or Firm* — Oliff PLC (57) ABSTRACT

A lighting apparatus which provides an heat dissipation effect, high output and large light emitting area including: housing having rectangular cylindrical shape obtained by forming belt-like body including plurality of holding bodies in rectangular cylindrical shape and connecting end portions of belt-like body formed in rectangular cylindrical shape; and circuit board mounted on inner surface of the housing and including a light source. The circuit board includes: mounting portion mounted on inner surface of the housing and having a surface provided with the light source; and connecting portion which connects mounting portions adjacent to each other in peripheral direction of the housing and is bendable at a corner of adjacent inner surfaces of the housing, and rear surface of mounting portion contacts inner surface of the holding body. Therefore, it is possible to provide lighting apparatus which provides an excellent heat dissipation effect, high output and large light emitting area.

6 Claims, 9 Drawing Sheets

(51) Int. Cl.
*G01N 21/88* (2006.01)
*F21V 23/02* (2006.01)
*F21V 23/00* (2015.01)
*H05K 1/18* (2006.01)
*F21V 29/507* (2015.01)
*H05K 1/14* (2006.01)

(52) U.S. Cl.
CPC ........ *G01N 21/8806* (2013.01); *F21V 23/001* (2013.01); *F21V 29/507* (2015.01); *F21Y 2107/50* (2016.08); *F21Y 2107/80* (2016.08); *H05K 1/148* (2013.01); *H05K 1/189* (2013.01); *H05K 2201/047* (2013.01); *H05K 2201/10106* (2013.01)

(58) Field of Classification Search
CPC . F21Y 2107/80; F21Y 2107/50; H05K 1/148; H05K 1/189; H05K 2201/047; H05K 2201/10106
USPC .......................................................... 362/382
See application file for complete search history.

(56) References Cited

U.S. PATENT DOCUMENTS

| | | | | |
|---|---|---|---|---|
| 6,299,337 B1* | 10/2001 | Bachl | .................... | F21S 48/215 |
| | | | | 257/E25.028 |
| 7,077,544 B2* | 7/2006 | Parker | .................. | A61M 21/02 |
| | | | | 362/231 |
| 9,163,792 B2* | 10/2015 | Weidman | .................. | F21L 4/02 |
| 2004/0037080 A1* | 2/2004 | Luk | ........................... | F21S 4/26 |
| | | | | 362/249.12 |
| 2004/0156210 A1* | 8/2004 | Pederson | ............. | B60Q 1/2611 |
| | | | | 362/545 |
| 2005/0207152 A1* | 9/2005 | Maxik | ..................... | F21K 9/135 |
| | | | | 362/231 |
| 2010/0314985 A1 | 12/2010 | Premysler | | |
| 2016/0123564 A1* | 5/2016 | Quilici | .................. | F21V 23/003 |
| | | | | 362/233 |

FOREIGN PATENT DOCUMENTS

| | | |
|---|---|---|
| JP | 2975893 B2 | 11/1999 |
| JP | 2000-269549 A | 9/2000 |
| JP | 2003-168305 A | 6/2003 |
| JP | 2005-150036 A | 6/2005 |
| JP | 2009-076250 A | 4/2009 |
| JP | 2009-277586 A | 11/2009 |
| JP | 2010-015810 A | 1/2010 |
| JP | 2010-055993 A | 3/2010 |
| JP | 2013-506955 A | 2/2013 |
| WO | 2009/013694 A2 | 1/2009 |

OTHER PUBLICATIONS

Jun. 17, 2014 Search Report issued in International Patent Application No. PCT/JP2014/061833.

Mar. 5, 2014 Office Action issued in Japanese Patent Application No. 2013-096859.

Aug. 16, 2016 Search Report issued in European Patent Application No. 14791575.5.

* cited by examiner

LIGHTING APPARATUS

TECHNICAL FIELD

The present invention relates to a lighting apparatus used as a lighting in product visual inspection and the like.

BACKGROUND ART

As a method of performing product surface inspection and the like, there is a generally known method in a related art in which a product is illuminated by using a lighting apparatus which emits light from a bottom surface, and inspection is carried out with reflected light thereof by performing visual check, photographing, or the like in the vicinity of the lighting apparatus.

There is a known lighting apparatus disclosed in Patent Literature 1 as an example of such a lighting apparatus. According to this lighting apparatus, a flexible substrate having an open ring shape is held in a planar state, and then LEDs are implanted all over the flexible substrate with soldering, and the plurality of LEDs is arranged on a recessed surface of a truncated cone by joining or closely holding one cut-off side and the other cut-off side of the flexible substrate such that the LEDs are positioned on the recessed surface side.

Further, there is a known technology disclosed in Patent Literature 2 as another example of the lighting apparatus for performing product surface inspection and the like. According to this lighting apparatus, three or more plate-like circuit boards are integrally connected in a longitudinal direction via foldable flexible members, a composite board is formed by mounting LED elements on at least one surface of the circuit boards, the composite substrate is folded between the circuit boards to form a hollow polygonal cylindrical shape, and an inner surface and/or an outer surface of the polygonal cylindrical body are formed as light emitting surfaces.

CITATION LIST

Patent Literature

Patent Literature 1: JP 2975893 B
Patent Literature 2: JP 2000-269549 A

SUMMARY OF INVENTION

Technical Problem

Meanwhile, according to the lighting apparatus of Patent Literature 1, when the flexible substrate is bent in the truncated cone shape, the flexible substrate is curved. Therefore, soldering that fixes the LEDs to the flexible substrate may be cracked, and this may cause malfunction of light operation.

Also, this kind of lighting apparatus is not suitable for inspecting whether a linear groove is correctly formed on a surface of a product to be inspected, for example. The reason is that light from the lighting apparatus is emitted to the linear groove from various directions because of a characteristic of the ring-like shape. Due to this characteristic, the light is not emitted along the linear groove, and this may cause unevenness of light in the linear groove. As a result, it becomes unclear whether the linear groove is correctly formed.

Therefore, a lighting apparatus having a rectangular cylindrical shape and capable of emitting the light along the linear groove is suitable in the inspection described above.

On the other hand, the lighting apparatus disclosed in Patent Literature 2 is a lighting apparatus having the rectangular cylindrical shape and the circuit board is prevented from being curved. Therefore, there is no possibility of causing malfunction due to the crack of the soldering and the like as described above.

However, according to this lighting apparatus, no light source such as an LED is provided at a flexible member capable of folding the circuit board. Therefore, unevenness of the light is caused on an inspection surface of a product to be inspected, and there may be a case where a minute flaw, a fault of finish, etc. on the inspection surface cannot be detected.

Additionally, in recent years, it is likely to use a so-called power LED having high light output because of acceleration of inspection, but no consideration is given to heat dissipation in the case of using the power LED having a large heat generation amount. In other words, Patent Literature 2 only discloses that the lighting apparatus is used while being fixed to an appropriate case, a frame, etc. by fixing means such as a screw, and does not disclose anything about heat dissipation.

The present invention is achieved in view of the above-described situations, and directed to providing a lighting apparatus which provides an excellent heat dissipation effect even in the case of using a light source having a large heat generation amount, and also has high output and a large light emitting area.

Solution to Problem

To achieve the above-mentioned objects, the lighting apparatus of the present invention provides a lighting apparatus including a circuit board and a holding body to hold the circuit board. In this lighting apparatus, the circuit board includes a plurality of mounting portions mounted with light sources, and a connecting portion which connects the mounting portions adjacent each other, is capable of energizing, and is having flexibility, and the holding body holds the circuit board in a state of directly contacting or indirectly contacting a rear surface of the mounting portion, and a housing is formed by mutually connecting end portions of the holding body.

Here, the circuit board is not limited to have an entire structure formed of the flexible substrate, including the mounting portion and the connecting portion, and a rigid substrate may be used as the mounting portion and a flexible substrate may be used to form the connecting portion to connect such rigid substrates.

As the circuit board having such a structure, a following structure may be preferable, for example: copper foil is formed on one surface of a resin substrate having flexibility and formed of polyamide resin, a wiring pattern is formed on this copper foil surface, a number of LEDs are provided as light sources, and further a thin film of aluminum or the like having excellent heat conductivity is formed on the other surface of the resin substrate. Preferably, the thin film of aluminum or the like is formed in a manner facing a region provided with the LEDs.

Further, the LED is preferably used as the light source, but a light source other than the LED may be used, too.

The "holding body" in the present invention is adapted to form a housing of the lighting apparatus, and preferably at least a portion of the circuit board contacting the mounting portion has excellent heat conductivity and rigidity, and more preferably the holding body has a heat conductivity rate larger than a heat conductivity rate of the mounting portion.

Further, the holding body is in the state of directly contacting or indirectly contacting the rear surface of the mounting portion, but note that "the state of indirectly contacting" means a state in which heat dissipating means (such as a heat dissipation sheet) is provided between the holding body and the rear surface of the mounting portion, and the holding body and the rear surface of the mounting portion contact the heat dissipation sheet respectively. As for a relation of the heat conductivity rate in the case of interposing the heat dissipating means, it is preferable that the heat dissipating means has the heat conductivity rate smaller than a holding frame and the mounting portion has the heat conductivity rate larger than the heat dissipating means.

Forming the housing with the holding body is not limited to connecting end portions of each of a plurality of holding bodies described later, and may be connecting the end portions of one belt-like holding body. In the case of the one belt-like holding body, a portion where the connecting portion of the circuit board is held in parallel has flexibility such that the holding body can be bent together with the connecting portion in the state of holding the circuit board.

According to the present invention, heat generated at the light sources is transferred to the holding body via the mounting portion and the heat is dissipated from the holding body because the rear surface of the mounting portion provided with the light sources contacts the holding body. Further, the light sources can be arranged in an entire inner surface of the holding body by mounting the mounting portion provided with the light sources on the inner surface of the holding body. As a result, high output and a large light emitting area can be achieved.

Therefore, it is possible to provide a lighting apparatus which provides an excellent heat dissipation effect even in the case of using the light source having a large heat generation amount, and also has high output and the large light emitting area.

In the above-described structure of the present invention, the holding body is preferably provided with a recessed portion to house the connecting portion.

In the case where a surface mounted with light source is oriented to an inner side of the housing, the recessed portion is preferably provided at a corner inside the housing. In the case where the surface mounted with the light sources is oriented to an outer side of the housing, the recessed portion is preferably provided at a corner outside the housing.

According to this structure, since the connecting portion is housed inside the recessed portion not provided with a light source, the light emitting surface can be continuously formed by disposing the adjacent mounting portions sufficiently close to each other without interfering with the connecting portion. Therefore, the light emitting area can be further increased by disposing the light sources all over the mounting portion while suppressing unevenness of the light at the connecting portion.

Further, according to the above-described structure of the present invention, the circuit board preferably includes a fixed portion projecting to the outside of the mounting portion, and the fixed portion is fixed to the holding body by physical fixing means.

Here, for example, fixing members such as a screw, a machine screw, and a nail can be used as the physical fixing means, but not limited thereto.

According to this structure, since the fixed portion projecting to the outside of the mounting portion is fixed to the holding body by the physical fixing means, the circuit board is prevented from being peeled off from the holding frame due to time degradation. Further, since the fixed portion projects to the outside of the mounting portion, the large area of the mounting portion can be secured. Therefore, the light emitting area can be further increased by disposing the light sources all over the mounting portion.

Further, in the above structure of the present invention, a head portion of the physical fixing means is preferably housed in the recessed portion.

According to the structure, the head of the physical fixing means does not interfere with the housing. Therefore, light leakage from clearance formed in the housing can be prevented.

Further, in the above structure of the present invention, the holding body includes an inserting portion into which a power cable to supply power to the circuit board is inserted, and preferably the power cable is pressed by mutually connecting the end portions of the holding body.

According to this structure, the power cable inserted into the inserting portion is pressed by mutually connecting the end portions of the holding body. As a result, clearance is prevented from being formed between the power cable and the housing. Therefore, light leakage to the outside of the housing can be prevented, and further the power cable is prevented from coming off from the housing.

Advantageous Effects of Invention

According to the present invention, it is possible to provide a lighting apparatus which provides an excellent heat dissipation effect even in the case of using the light source having a large heat generation amount, and also has high output and the large light emitting area.

DESCRIPTION OF EMBODIMENTS

Embodiments of the present invention will be described below with reference to the drawings.

Figure 1:
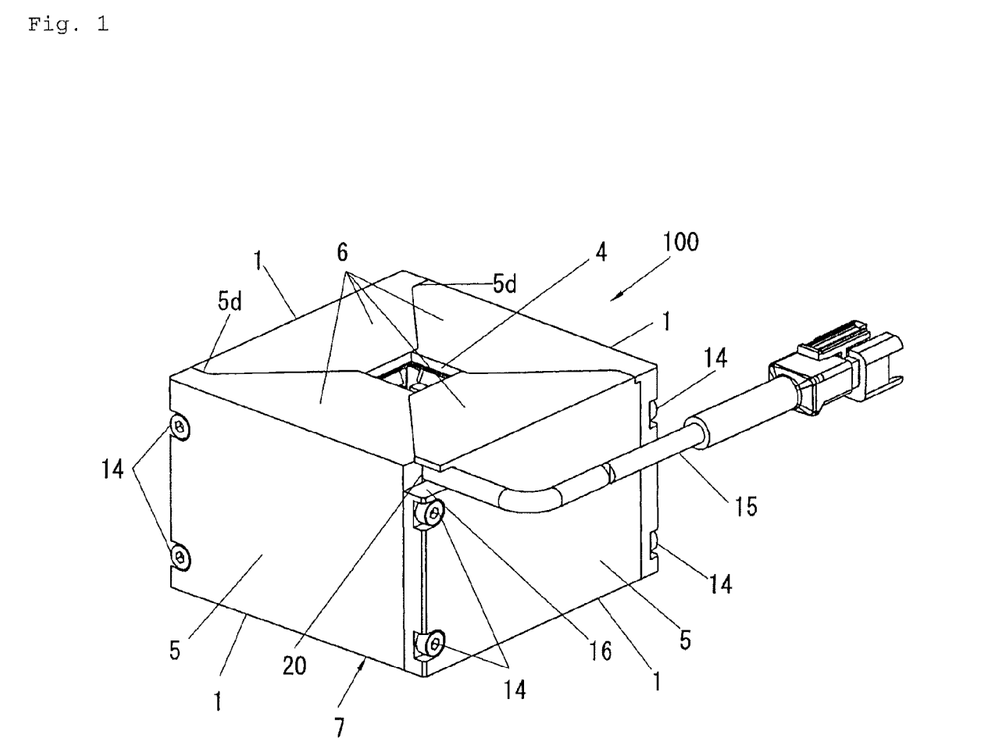
FIG. 1 is a diagram illustrating an irradiation apparatus according to an embodiment of the present invention, and is a perspective view of the lighting apparatus.
Figure 2:
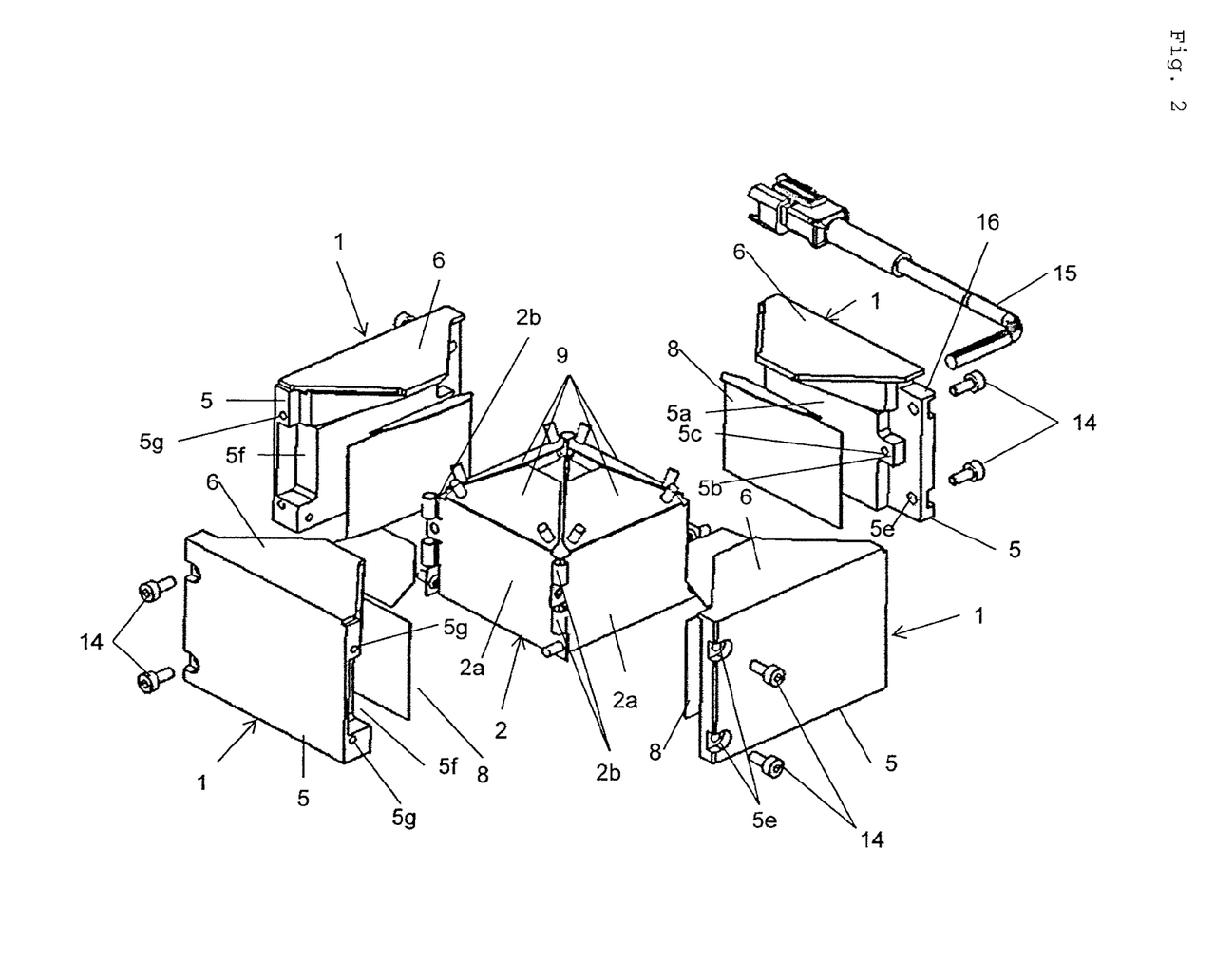
FIG. 2 is an exploded perspective view of the lighting apparatus according to the same embodiment.

FIGS. 1 and 2 are diagrams illustrating an irradiation apparatus according to an embodiment of the present invention. FIG. 1 is a perspective view and FIG. 2 is an exploded perspective view.

A lighting apparatus 100 according to the present embodiment is used as a lighting in product visual inspection and the like, and includes a holding body 1 and a circuit board 2 held by the holding body 1 and provided with a light source 3.

The holding body 1 is formed of side plate portions 5 and upper plate portions 6, and a housing 7 having a square cylindrical shape is formed by connecting end portions of four holding bodies 1. Further, an opening 4 is formed by the upper plate portions 6 by mutually connecting end portions of the four holding bodies 1. The opening 4 is used when inspection is performed by visual check, photographing, or the like. Further, the lighting apparatus 100 includes a power cable 15 to supply power to the circuit board 2, and the power cable 15 extends from the housing 7.

The circuit board 2 is formed of a mounting portion 2a and a later-described connecting portion 2b which is capable of energizing and has flexibility. Further, the holding body 1 holds the circuit board 2 in a state of contacting a rear surface of the mounting portion 2a. Further, a heat conductivity rate of the holding body 1 is larger than a heat conductivity rate of the mounting portion 2a.

Figure 3:
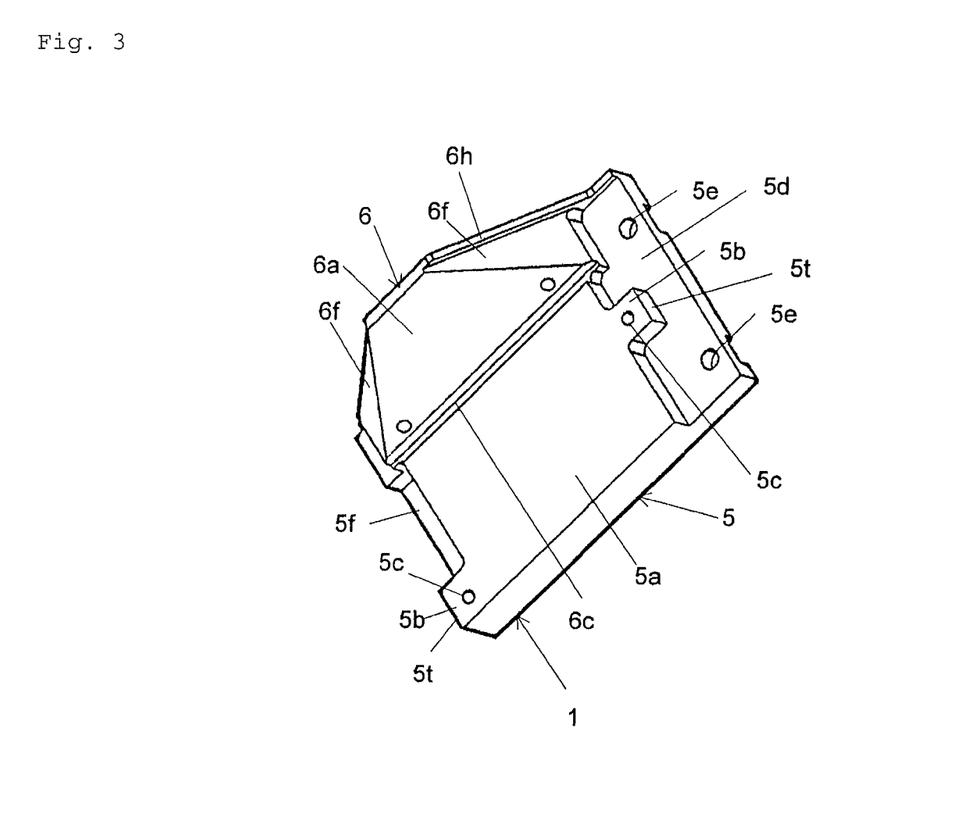
FIG. 3 is a perspective view illustrating a holding body according to the same embodiment.

As illustrated in FIGS. 2 and 3, the side plate portion 5 is formed in a substantially rectangular plate-like shape, and a mounting surface 5a of the side plate portion 5 is formed on an inner surface side facing the inside of the housing 7. Further, the mounting portion 2a of the circuit board 2 is set so as to closely contact the mounting surface 5a, interposing a heat dissipation sheet 8. Further, fixing surfaces 5b, 5b respectively projecting from both side portions of the mounting surface 5a to the outside are formed on an inner surface side of the side plate portion 5, and screw holes 5c, 5c are formed on the fixing surfaces 5b, 5b. The fixing surfaces 5b, 5b are formed on an upper surfaces of projecting portions 5t, 5t, and the fixing surfaces 5b, 5b are formed at positions substantially point-symmetric with respect to a center of the mounting surface 5a by disposing the projecting portions 5t, 5t at positions substantially point-symmetric with respect to the center of the mounting surface 5a, and further the fixing surfaces 5b, 5b are formed in the same level as the mounting surface 5a.

Furthermore, on the inner surface side of the side plate portion 5, an abutment object surface 5d is formed on one side of the mounting surface 5a that has a predetermined level difference 5d from the mounting surface 5a, and holes 5e, 5e penetrating the abutment object surface 5d from an outer surface of the side plate portion 5 are formed apart from each other in a short side direction of the side plate portion 5. A lateral width of the abutment object surface 5d (long side direction of the side plate portion 5) is wider than a maximum thickness of the side plate portion 5. One projecting portions 5t out of the two projecting portions 5t, 5t is formed on the abutment object surface 5d.

Further, a recessed portion 5f is formed on the other side of the mounting surface 5a on the inner surface side of the side plate portion 5. The recessed portion 5f is used to house the connecting portion 2b which is bent as described later, and has a shape obtained by cutting off a side end portion of the side plate portion 5 to have an L-shape cross-section. A vertical dimension thereof (dimension in the short side direction of the holding body 1) is sufficiently longer than a width of the connecting portion 2b. Further, a bottom surface of the recessed portion 5f is positioned on a more outer surface side of the side plate portion 5 than the abutment object surface 5d. In other words, a depth of the recessed portion 5f from the mounting surface 5a is deeper than the abutment object surface 5d. The other projecting portion 5t is formed under the recessed portion 5f.

Further, a left-side end surface where the recessed portion 5f of the side plate portion 5 is formed is an abutment surface to abut against the abutment object surface 5d of the side plate portion 5 adjacent thereto when the side plate portions 5, namely, the holding bodies 1 are connected in a square cylindrical shape. On this side end surface (abutment surface), screw holes 5g, 5g are formed apart from each other in the short side direction of the side plate portion 5 at the positions interposing the recessed portion 5f (refer to FIG. 2).

As illustrated in FIGS. 1 to 3, the upper plate portion 6 includes amounting surface 6a facing the inner side of the housing 7, and a groove 6c is formed between the mounting surface 6a and the mounting surface 5a.

Further, the upper plate portion 6 includes triangular abutment surfaces 6f, 6f, and the abutment surfaces 6f, 6f of the adjacent upper plate portions 6, 6 abut against each other when the side plate portions 5 are connected in the square cylindrical shape.

Furthermore, the upper plate portion 6 includes a receiving surface 6g that has a predetermined level difference from an upper surface (refer to FIG. 7), and further includes a protruding portion 6h protruding from the upper surface. Further, when the abutment surfaces 6f, 6f of the adjacent upper plate portions 6, 6 abut against each other, the protruding portion 6h abut against the receiving surface 6g, thereby preventing light leakage from between the abutment surfaces 6f, 6f.

Figure 4:
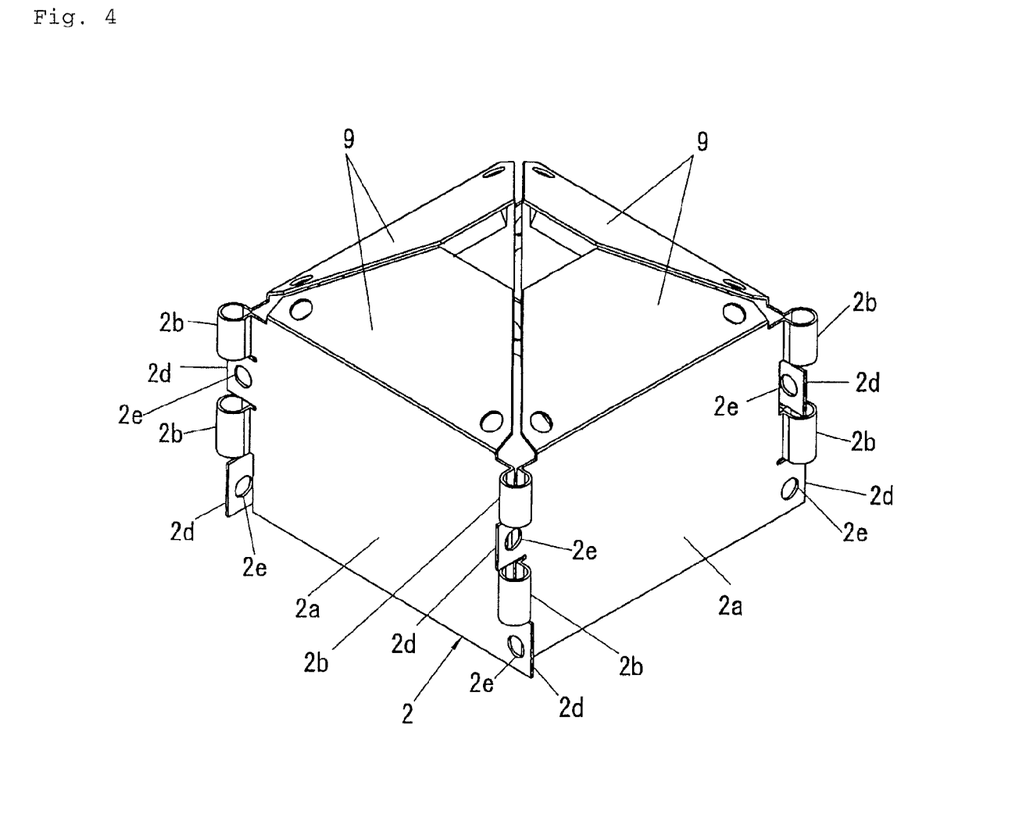
FIG. 4 is a perspective view illustrating a state in which a circuit board is formed in a square cylindrical shape according to the same embodiment.
Figure 5:
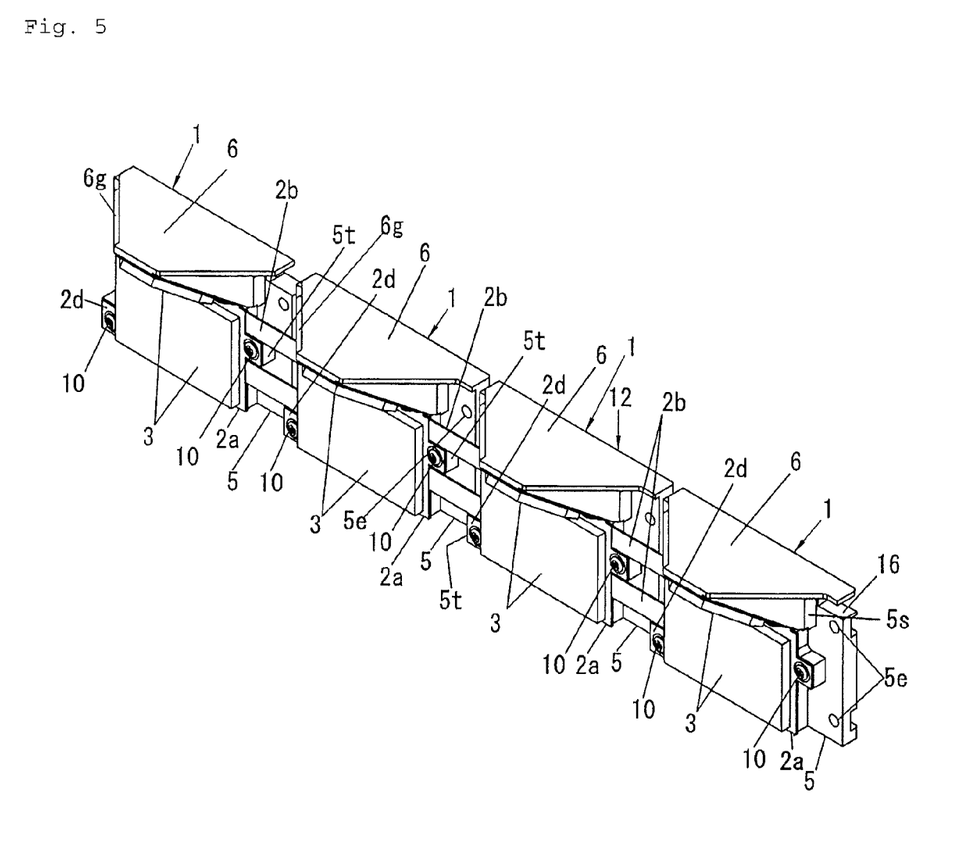
FIG. 5 is a perspective view of a belt-like body according to the same embodiment.
Figure 6:
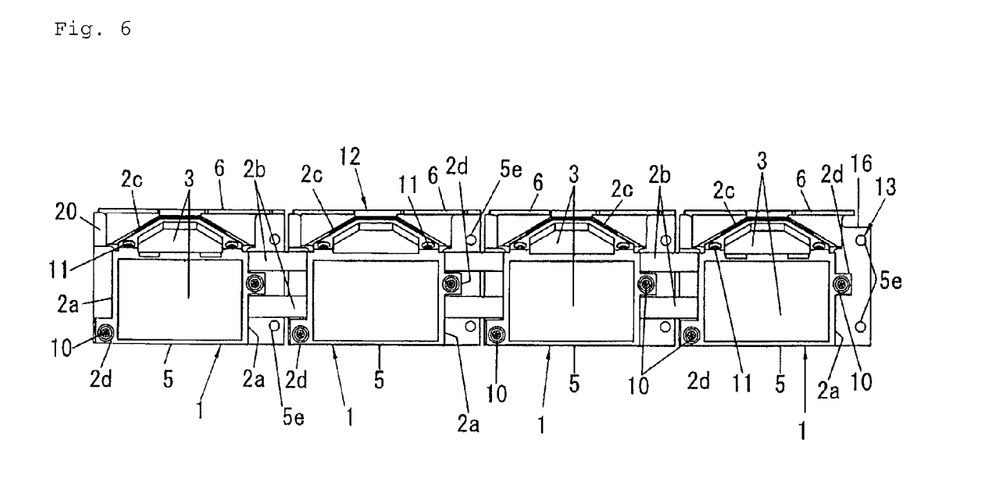
FIG. 6 is a front view of the belt-like body according to the same embodiment.

The circuit board 2 is formed of a soft flexible substrate, and includes four of the mounting portions 2a and the connecting portion 2b that has flexibility and mutually connects the adjacent mounting portions 2a, 2a in an energizable manner as illustrated in FIGS. 4 to 6. The mounting portion 2a is formed in a rectangular shape, and formed in a size almost equal to the mounting surface 5a. Two of the connecting portions 2b are formed in parallel in belt-like shapes between the adjacent mounting portions 2a, 2a. The connecting portions 2b are bendable at a corner between adjacent inner surfaces of the housing 7, namely, at the corner on the inner surface sides of the adjacent holding bodies 1, 1.

Further, the circuit board 2 includes the fixed portions 2d, 2d projecting to the outside of the mounting portion 2a, and a hole 2e is formed at the fixed portion 2d (refer to FIG. 4). The fixed portions 2d, 2d are positioned substantially point-symmetric with respect to the center of the mounting portion 2a, and further are formed at positions corresponding to the fixing surfaces 5b.

Further, the lighting apparatus 100 includes a trapezoidal circuit board 9 having a substantially trapezoid shape. The trapezoidal circuit board 9 is mounted on the mounting surface 6a of the upper plate portion 6, and the trapezoidal circuit board 9 is electrically connected to the circuit board 2.

Further, the light sources 3 are disposed on the mounting portion 2a of the thus structured circuit board 2 and the trapezoidal circuit board 9 respectively. The light source 3 includes a number of LEDs (not illustrated) mounted all over the mounting portion 2a and the trapezoidal circuit board 9 respectively, and includes a translucent diffuser panel that covers the multiple LEDs entirely. Therefore, the light sources 3 are disposed on a substantially entire area of the mounting portion 2a and the trapezoidal circuit board 9, thereby achieving a sufficiently large light emitting area.

As illustrated in FIGS. 5 and 6, the circuit board 2 including such light sources 3 have the four holding bodies 1 arranged on right and left side in parallel, and the circuit boards 2 are arranged on the right and left sides of these four holding bodies 1 in a manner extending from the four holding bodies 1. Then, the four holding bodies 1 are connected in the belt-like shape by fixing the circuit boards 2 to the holding bodies 1.

In the case of fixing the circuit board 2 to the holding body 1, each mounting portion 2a closely contacts the mounting surface 5a of the side plate portion 5 of each holding body 1 while interposing the heat dissipation sheet 8, and further each trapezoidal circuit board 9 closely contacts the mounting surface 6b of each upper plate portion 6 while interposing the heat dissipation sheet 8. Additionally, the fixed portion 2d of the circuit board 2 is set to the fixing surface 5b of the side plate portion 5, and a screw 10 (physical fixing means) is inserted into the hole 2e of the fixed portion 2d and screwed into the screw hole 5c of each fixing surface 5b, thereby fixing the circuit board 2 to the holding body 1.

In this state, the connecting portions 2b, 2b are arranged so as to connect the side plate portions 5, 5 of the adjacent holding bodies 1, 1. In FIGS. 5 and 6, the connecting portion 2b on an upper side has an upper hem abut against lower portions of the upper plate portions 6, 6 and has a lower hem abut against the projecting portion 5t to form the fixing surface 5b, thereby limiting vertical movement. Further, the connecting portion 2b on a lower side has an upper hem and a lower hem respectively abut against the projecting portions 5t, 5t to form the fixing surfaces 5b, 5b disposed on upper and lower sides, thereby limiting vertical movement.

Figure 7:
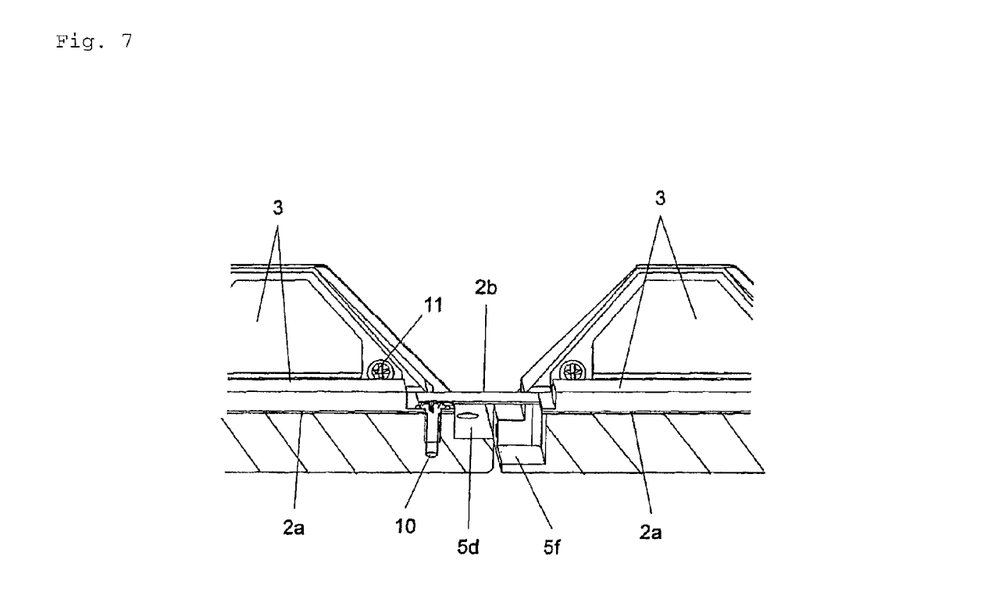
FIG. 7 is a cross-sectional view of a connecting portion of the belt-like body according to the same embodiment.

Further, as illustrated in FIG. 7, the connecting portion 2b is disposed above the recessed portion 5f of one of the side plate portions 5 and the abutment object surface 5d of the other side plate portion 5. Further, when the end portions of the holding bodies 1, 1 are connected each other, the recessed portion 5f is formed between the end portions of the side plate portions 5, 5 by making the side end surface of one side plate portion 5 (on the right side in FIG. 7) abut against the abutment object surface 5d of the other side plate portion 5 such that the bent connecting portion 2b is housed in the recessed portion 5f.

A belt-like body 12 formed by thus connecting the four holding bodies 1 are assembled in the square cylindrical shape, and connecting means 13 to connect the end portions is provided at both end portions of the belt-like body 12.

The connecting means 13 is formed of the hole 5e formed on the abutment object surface 5d of the holding body 1 positioned at one end portion of the belt-like body 12, the screw hole 5g formed on the side end surface of the holding body 1 positioned at the other end portion of the belt-like body 12, and a holding body connecting screw 14 to be inserted into the hole 5e and screwed into the screw hole 5g (refer to FIGS. 1 and 2).

In the case of assembling the four holding bodies 1 of the above-described belt-like body 12 in the square cylindrical shape, the four holding bodies 1 are formed in the square cylindrical shape by bending the connecting portions 2b of the circuit board 2 such that the surfaces mounted with the light sources 3 face the inside, and further by making the bent connecting portions 2b project outward (refer to FIG. 2). Further, since the upper plate portions 6 of the holding bodies 1 are integrally formed with the side plate portion 5, the upper plate portions 6 are arranged in the rectangular plate-like shape having the opening 4 at the center in a planar view by arranging the side plate portions 5 in the square cylindrical shape.

In the case of arranging the holding bodies 1 in the square cylindrical shape, one side plate portion 5 out of the side plate portions 5, 5 of the adjacent holding bodies 1, 1 has the side end surface abut against the abutment object surface 5d of the other side end surface 5, and then the adjacent side plate portions 5, 5 are mutually connected and fixed by inserting the holding body connecting screw 14 into the hole 5e formed on the abutment object surface 5d and screwing the same into the screw hole 5g formed on the side end surface.

Figure 8:
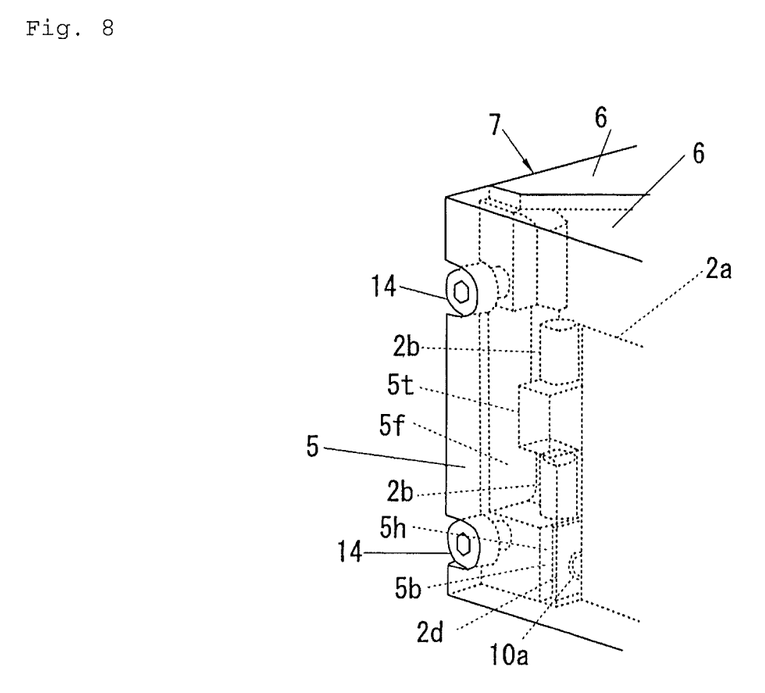
FIG. 8 is a perspective view including an internal structure of a corner of a housing according to the same embodiment.

As a result, the recessed portion 5f is formed at the corner of the adjacent inner surfaces of the housing 7 by the recessed portion 5f because the recessed portion 5f is formed on the side end portion of one of the side plate portions 5 as illustrated in FIG. 8.

On the other hand, since the connecting portion 2b of the belt-like body 12 is disposed above the recessed portion 5f of one of the side plate portions 5 as illustrated in FIG. 7, when the connecting portion 2b is bent, the connecting portion 2b becomes a substantially cylindrical shape as illustrated in FIG. 2 and the connecting portion 2b having the substantially cylindrical shape is housed in the recessed portion 5f as illustrated in FIG. 8. Further, as described above, vertical movement of the connecting portion 2b (vertical direction in FIGS. 5 and 6) is limited by the upper plate portion 6 and the projecting portion 5t. Therefore, when the connecting portion 2b is bent, the connecting portion 2b becomes the substantially cylindrical shape without escaping in the vertical direction and can be smoothly housed in the recessed portion 5f.

Figure 9:
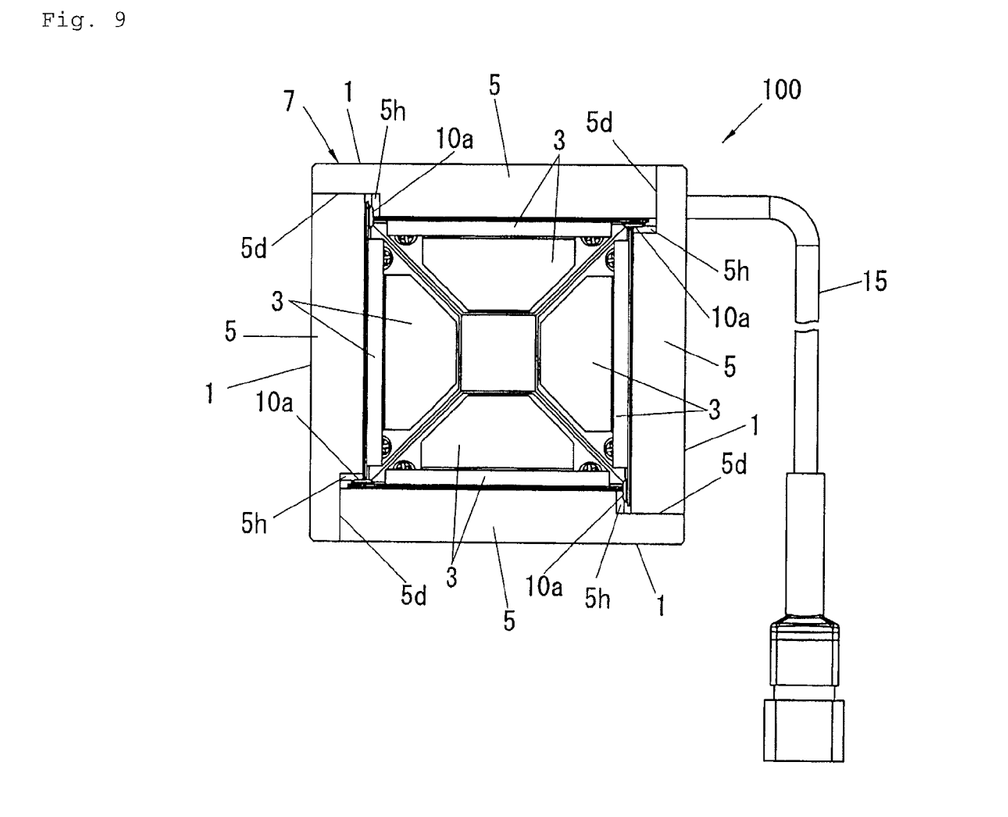
FIG. 9 is a bottom view of the lighting apparatus according to the same embodiment.
Figure 10:
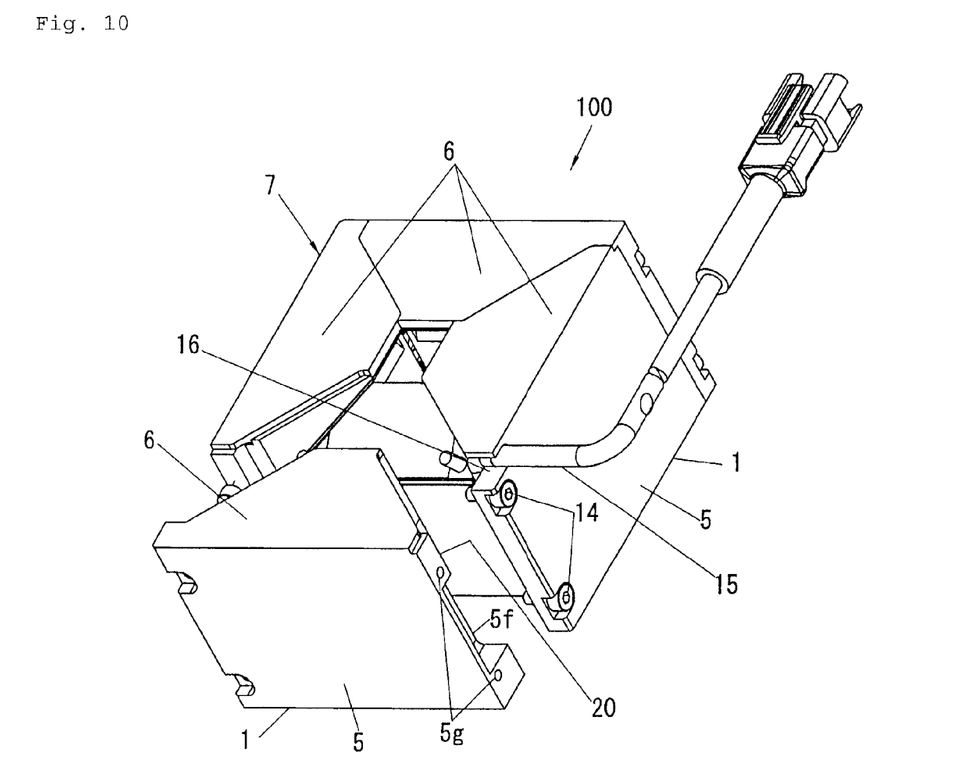
FIG. 10 is a perspective view of the lighting apparatus, illustrating a state in which one holding body is detached.

Further, the lateral width of the abutment object surface 5d of the side plate portion 5 is wider than the maximum thickness of the side end surface of the side plate portion 5. Therefore, as illustrated in FIG. 9, the side end surface of one of the side plate portions 5 abuts against the abutment object surface 5d of the other side plate portions 5, thereby providing the recessed portion 5h at the corner between the adjacent inner surfaces of the housing 7. Therefore, the fixed portion 2d is housed in the recessed portion 5h, and further a head portion 10a of a fixing surface fixing screw 10 to fix the fixed portion 2d to the fixing surface 5b is housed in the recessed portion 5h.

Additionally, the adjacent upper plate portions 6, 6 allow the abutment surfaces 6f, 6f to abut against each other, and further one protruding portion 6h of one of the upper plate portions 6 abuts against and is joined to the receiving surface 6g of the other upper plate portion 6, thereby preventing light leakage from between the abutment surfaces 6f, 6f.

After the adjacent holding bodies 1, 1 of the belt-like body 12 are connected and fixed each other, both end portions of the belt-like body 12 are connected by the connecting means 13. In other words, after the side end surface of the side plate portion 5 of the holding body 1 located on one end portion side of the belt-like body 12 connected in the square cylindrical shape is made to abut against the abutment object surface 5d of the side plate portion 5 of the holding body 1 positioned on the other side portion side, the holding body connecting screw 14 is inserted into the hole 5e formed on the abutment object surface 5d and screwed into the screw hole 5g formed on the side end surface, thereby mutually connecting the end portions of the belt-like body 12.

Further, according to the present embodiment, as illustrated in FIGS. 1, 2, 5, 6, and 10, an inserting portion 16 to insert the power cable 15 from the outside to the inside of the housing 7 is provided on an upper portion of the side end portion of one of the side plate portions 5 connected by the connecting means 13. The power cable 15 is used to supply power to the circuit board 2. The inserting portion 16 has a groove-like shape and is formed on the side end surface of the side plate portions, and a width of the inserting portion 16 is substantially equal to a diameter of the power cable 15. Further, the power cable 15 extends up to the circuit board 2 on the abutment object surface 5*d* and is connected to the circuit board 2 after being inserted into the inserting portion 16 from the outside.

Furthermore, the power cable 15 inserted into the inserting portion 16 is pressed by mutually connecting the end portions of the holding bodies 1, 1. In other words, the power cable 15 is pressed against the holding body 1 by a pressing portion 20. More specifically, the pressing portion 20 is formed of a surface 20 orthogonal to the side end surface of the side plate portion 5 adjacent to the side plate portion 5 formed with the inserting portion 16 (refer to FIGS. 1, 6, and 10), and the power cable 15 is pressed against the holding body 1 by this surface 20. A region of the holding body 1 against which the power cable 15 is pressed is a surface 5*s* orthogonal to the abutment object surface 5*d* of the side plate portion 5 formed with the inserting portion 16 as illustrated in FIG. 5.

In the case of assembling the lighting apparatus having the above-described structure, the four holding bodies 1 are arranged in one direction in parallel to form the belt-like body 12, and the circuit boards 2 having the belt-like shape and provided with the light sources are arranged in the belt-like body 12, extending in the parallel arrangement direction of the side plate portions 5 as illustrated in FIGS. 5 and 6. After that, the circuit boards 2 are fixed to the side plate portions 5, and further the trapezoidal circuit boards 9 are fixed to the upper plate portions 6.

Next, the square cylindrical shape is formed as illustrated in FIGS. 1 and 9 by folding (bending), at the connecting portions 2*b*, the belt-like body 12 mounted with the above circuit boards 2 and trapezoidal circuit boards 9. Then, the adjacent holding bodies 1, 1 are mutually connected, and the side plate portion 5 positioned on one end portion side of the belt-like body 12 and formed with the inserting portion 16 is connected to the side plate portion 5 positioned on the other end portion side of the belt-like body 12 by the connecting means 13. At this point, the power cable 15 is preliminarily inserted into the inserting portion 16, and when the end portions of the adjacent holding bodies 1, 1 are mutually connected by the connecting means 13, the power cable 15 is pressed against the surface 5*s* of the side plate portion 5 by the pressing portion 20.

As described above, according to the present embodiment, the rear surface of the mounting portion 2*a* provided with the light sources 3 closely contacts the mounting surface 5*a* of the holding body 1 via the heat dissipation sheet 8. Therefore, heat generated at the light sources 3 can be transferred to the holding body 1 via the mounting portion 2*a* and the heat dissipation sheet 8, and dissipated to the outside from the holding body 1. Further, since the mounting portion 2*a* provided with the light sources 3 is mounted on the mounting surface 5*a* of the holding body 1, the light sources 3 can be arranged on an entire inner surface of the holding body 1. As a result, high output and a large light emitting area can be obtained.

Therefore, even in the case of using the light source having a large heat generation amount, it is possible to provide the lighting apparatus having an excellent heat dissipation effect and having high output and a large light emitting area.

Further, the recessed portions 5*f* are provided at the corners of the mounting surfaces 5*a*, 5*a* of the side plate portions 5, 5, of the adjacent holding bodies 1, 1, and the connecting portions 2*b* not including the light source of the circuit board 2 are housed in the recessed portions 5*f*. Therefore, the light emitting surface can be continuously formed by disposing the adjacent mounting portions 2*a*, 2*a* sufficiently close to each other on the adjacent inner surfaces (mounting surfaces 5*a*) of the housing 7 without interfering with connecting portions 2*b*. Therefore, the light emitting area can be further increased by disposing the light sources all over the mounting portions 2*a* while suppressing unevenness of the light at the connecting portions 2*b*.

Further, since the circuit board 2 includes the fixed portion 2*d* projecting to the outside of the mounting portion 2*a*, and the fixed portion 2*d* is fixed to the fixing surface 5*b* of the side plate portion 5 by the screw (physical fixing means) 10, the circuit board 2 is prevented from being peeled off from a holding frame due to time degradation. Further, since the fixed portion 2*d* projects to the outside of the mounting portion 2*a*, the large area of the mounting portion 2*a* can be secured and the light emitting area can be further increased by disposing the light sources 3 all over the mounting portion 2*a*.

Additionally, since the head portion 10*a* of the fixing surface fixing screw 10 is housed in the recessed portion 5*h*, the head portion 10*a* does not interfere with the housing 7. Therefore, light leakage from clearance formed in the housing 7 can be prevented.

Further, clearance is prevented from being formed between the power cable 15 and the housing 7 because the power cable 15 inserted into the inserting portion 16 is pressed against the surface 5*s* of the side plate portion 5 by the pressing portion 20. Therefore, light leakage to the outside of the housing can be prevented, and also the power cable 15 can be prevented from coming off from the housing 7.

Furthermore, since the circuit board 2 is formed of the flexible substrate, wiring between the mounting portions 2*a*, 2*a* is not needed, and also since the connecting portion 2*b* of the circuit board 2 is formed thinner than the mounting portion 2*a*, the circuit boards 2 can be easily formed in the square cylindrical shape and assembly is simplified.

Moreover, vertical movement of the connecting portion 2*b* on the upper side of the circuit board 2 is limited because the upper hem thereof abuts against the lower portions of the upper plate portions 6, 6 and the lower hem thereof abuts against the projecting portion 5*t* to form the fixing surface 5*b*, and also vertical movement of the connecting portion 2*b* on the lower side is limited because the upper and lower hems thereof respectively abut against the projecting portions 5*t* to form the fixing surfaces 5*b*, 5*b* located above and below. Therefore, the connecting portions 2*b*, 2*b* can be prevented from escaping in the vertical direction when the mounting portion 2*a* is mounted on the mounting surface 5*a* of the side plate portion 5 and when the belt-like body 12 is folded in the square cylindrical shape. As a result, the mounting portion 2*a* can be prevented from floating from the mounting surface 5*a* due to escaping movement.

Further, since the connecting portion 2*b* is disposed above the recessed portion 5*f* of the side plate portion 5 in the belt-like body 12, the connecting portion 2*b* is bent in the cylindrical shape and housed in the recessed portion 5*f* when the belt-like body 12 is folded in the square cylindrical shape. Therefore, the connecting portion 2b does not interfere with the mounting portion 2a, and further the mounting portion 2a can be prevented from floating.

Additionally, since the upper plate portion 6 includes the receiving surface 6g and also includes the protruding portion 6h, light leakage from between the abutment surfaces 6f, 6f can be prevented by the protruding portion 6h abutting against the receiving surface 6g when the adjacent abutment surfaces 6f, 6f of the adjacent upper plate portions 6, 6 abut against each other.

Further, since the groove 6c is formed between the mounting surface 5a to be mounted with the mounting portion 2a and the mounting surface 6b to be mounted with the trapezoidal circuit board 9 (refer to FIG. 5), the bent connecting portion between the mounting portion 2a and the trapezoidal circuit board 9 can escape to the groove 6c. As a result, the mounting portion 2a and the trapezoidal circuit board 9 can be prevented from floating.

Moreover, since the belt-like body 12 is formed by connecting plural (four) holding bodies 1, the lighting apparatus formed in a rectangular cylindrical shape having desired number of corners can be manufactured by increasing/reducing the number of holding bodies 1 and also by increasing/reducing a length of the circuit board 2.

Meanwhile, according to the present embodiment, an example in which the housing 7 is formed in the square cylindrical shape has been described, but the housing 7 may also be formed in a triangular cylindrical shape or a polygonal cylindrical shape of a pentagon and more polygonal shapes in the present invention.

Further, the upper plate portions 6 are integrally formed at the upper end portions of the side plate portions 5 in the present embodiment, but the upper plate portion 6 may also be omitted in the present invention, if necessary.

Furthermore, while the exemplary case in which the belt-like body 12 including the plural (four) holding bodies 1 is formed in the rectangular cylindrical shape (square cylindrical shape) has been described in the present embodiment, but not limited thereto, for example, the belt-like body including one holding body 1 may be formed in the rectangular cylindrical shape.

REFERENCE SIGNS LIST

1 Holding body
2 Circuit board
2a Mounting portion
2b Connecting portion
2d Fixed portion
3 Light source
5 Side plate portion
5a Mounting surface
5b Fixing surface
7 Housing
12 Belt-like body
13 Connecting means
15 Power cable
16 Inserting portion
5f, 5h Recessed portion
20 Pressing portion

The invention claimed is:

1. A lighting apparatus, comprising:
a circuit board including a plurality of mounting portions where light sources are mounted and a connecting portion which connects the mounting portions adjacent each other, is capable of energizing, and has flexibility; and
a plurality of holding bodies configured to hold the circuit board in a state of directly contacting or indirectly contacting a rear surface of the mounting portions, a housing being formed by mutually connecting end portions of the holding bodies,
wherein the connecting portion is bendable and has a substantially cylindrical shape, at a corner between adjacent inner surfaces of the holding bodies.

2. The lighting apparatus according to claim 1, wherein the circuit board includes a fixed portion projecting to the outside of the mounting portions, and the fixed portion is fixed to the holding bodies by physical fixing means.

3. The lighting apparatus according to claim 1, wherein one of the holding bodies is provided with an inserting portion into which a power cable to supply power to the circuit board is inserted, and the power cable is pressed by mutually connecting end portions of the holding body.

4. A lighting apparatus, comprising:
a circuit board including a plurality of mounting portions where light sources are mounted and a connecting portion which connects the mounting portions adjacent each other, is capable of energizing, and has flexibility; and
a plurality of holding bodies configured to hold the circuit board in a state of directly contacting or indirectly contacting a rear surface of the mounting portions, a housing being formed by mutually connecting end portions of the holding bodies,
wherein the holding bodies are provided with a recessed portion configured to house the connecting portion, and the recessed portion does not house the light sources.

5. The lighting apparatus according to claim 4, wherein the circuit board includes a fixed portion projecting to the outside of the mounting portions, and the fixed portion is fixed to the holding bodies by physical fixing means.

6. The lighting apparatus according to claim 5, wherein a head portion of the physical fixing means is housed in the recessed portion.

* * * * *